(12) United States Patent
Ayene (10) Patent No.: US 8,697,391 B2
(45) Date of Patent: Apr. 15, 2014

(54) METHOD OF DETERMINING CELL NUMBER OR VIABILITY USING HYDROXYETHYLDISULFIDE

(75) Inventor: Iraimoudi S. Ayene, Newtown Square, PA (US)

(73) Assignee: Lankenau Institute for Medical Research, Wynnewood, PA (US)

(*) Notice: Subject to any disclaimer, the term of this patent is extended or adjusted under 35 U.S.C. 154(b) by 0 days.

(21) Appl. No.: 13/320,602

(22) PCT Filed: May 14, 2010

(86) PCT No.: PCT/US2010/034899
§ 371 (c)(1),
(2), (4) Date: Feb. 1, 2012

(87) PCT Pub. No.: WO2010/132771
PCT Pub. Date: Nov. 18, 2010

(65) Prior Publication Data
US 2012/0142041 A1    Jun. 7, 2012

Related U.S. Application Data

(60) Provisional application No. 61/290,084, filed on Dec. 24, 2009, provisional application No. 61/261,521, filed on Nov. 16, 2009, provisional application No. 61/178,929, filed on May 15, 2009.

(51) Int. Cl.
*C12Q 1/06*     (2006.01)
*C12Q 1/04*     (2006.01)

(52) U.S. Cl.
USPC ............................................. 435/39; 435/29

(58) Field of Classification Search
CPC .............. C12Q 1/02; C12Q 1/04; C12Q 1/06; C12Q 2304/20
See application file for complete search history.

(56) References Cited

U.S. PATENT DOCUMENTS

| | | | |
|---|---|---|---|
| 6,037,336 A | 3/2000 | Hausheer et al. | |
| 6,504,049 B1 | 1/2003 | Kochat | |
| 6,552,060 B1 | 4/2003 | Kirkpatrick | |
| 6,596,320 B1 | 7/2003 | Hausheer | |
| 7,169,412 B2 | 1/2007 | Kozhemyakin et al. | |
| 2003/0211514 A1 | 11/2003 | Penninger et al. | |
| 2004/0116496 A1 | 6/2004 | Kirkpatrick et al. | |
| 2010/0298412 A1 | 11/2010 | Ayene | |

FOREIGN PATENT DOCUMENTS

| | | |
|---|---|---|
| EP | 0 656 360 A1 | 6/1995 |
| WO | 99/20264 | 4/1999 |
| WO | 01/62259 | 8/2001 |
| WO | 2005/007108 | 1/2005 |
| WO | 2007/041546 | 4/2007 |
| WO | 2009/067489 | 5/2009 |

OTHER PUBLICATIONS

Biaglow et al. "A Method for Measuring Disulfide Reduction by Cultured Mammalian Cells: Relative Contributions of Glutathione-Dependent and Glutathione-Independent Mechanisms" Analytical Biochemistry, 281, 2000, 77-86.*
Afzal-Ahmed et al. "Preeclampsia inactivates glucose-6-phosphate dehydrogenase and impairs redox status of erythrocytes and fetal endothelial cells" Free Radical Biology & Medicine, 42, 2007, 1781-1790.*
Pi et al. "Evidence for Induction of Oxidative Stress Caused by Chronic Exposure of Chinese Residents to Arsenic Contained in Drinking Water" Environmental Health Perspectives, vol. 110 Issue 4, Apr. 2002, 331-336.*
Biaglow, J.E. et al. "Role of vicinal protein thiols in radiation and cytotoxic responses." Radiat Res. Mar. 2006;165 (3):307-17.
Biaglow, J.E., et al. "G6PD deficient cells and the bioreduction of disulfides: effects of DHEA, GSH depletion and phenylarsine oxide." Biochem Biophys Res Commun. Jul. 14, 2000;273(3):846-52.
Biaglow, J.E. et al. "Radiation response of cells during altered protein thiol redox." Radiat Res. Apr. 2003;159 (4):484-94.
Ayene, I., et al. "Mutation in G6PD gene leads to loss of cellular control of protein glutathionylation: mechanism and implication." J Cell Biochem. Jan. 1, 2008;103(1):123-35.
Ayene, I., et al. "Oxidation of cellular thiols by hydroxyethyldisulphide inhibits DNA double-strand-break rejoining in G6PD deficient mammalian cells." Int J Radiat Biol. Nov. 2000;76(11):1523-31.
Li, J., et al. "Glucose deprivation increases nuclear DNA repair protein Ku and resistance to radiation induced oxidative stress in human cancer cells." Cell Biochem Funct. Mar. 2009;27(2):93-101.
Ayene, I.S., et al. "Mutation in the glucose-6-phosphate dehydrogenase gene leads to inactivation of Ku DNA end binding during oxidative stress." J Biol Chem. Mar. 22, 2002;277(12):9929-35. Epub Jan. 11, 2002.
Bernstam, L., et al. "Molecular aspects of arsenic stress." J Toxicol Environ Health B Crit Rev. Oct.-Dec. 2000;3 (4):293-322.
Biaglow, J.E., et al. "Radiation response of cells during altered protein thiol redox." Radiat Res. Apr. 2003,159 (4):484-94.
Sharan, R.N., et al. "2-Mercaptopropionylglycine affords enhanced radioprotection after a liposome encapsulation." J Radiat Res (Tokyo). Mar. 1995;36(1):31-7.
Boven, E., et al. "Phase I and pharmacokinetic study of the novel chemoprotector BNP7787 in combination with cisplatin and attempt to eliminate the hydration schedule." Br J Cancer. May 9, 2005;92(9):1636-43.
Wouters, A., et al. "Review: implications of in vitro research on the effect of radiotherapy and chemotherapy under hypoxic conditions." Oncologist. Jun. 2007;12(6):690-712.
Yokomizo, A., et al. "Cellular levels of thioredoxin associated with drug sensitivity to cisplatin, mitomycin C, doxorubicin, and etoposide." Cancer Res. Oct. 1, 1995;55(19):4293-6.

(Continued)

*Primary Examiner* — Jon P Weber
*Assistant Examiner* — Charles Zoltan Constantine
(74) *Attorney, Agent, or Firm* — Robert C. Netter, Jr.; Dann, Dorfman, Herrell & Skillman (57) ABSTRACT

A method for determining the percentage of live cells or viability of cells in a sample is disclosed. In this method, a cell-containing sample is contacted with hydroxyethyldisulfide and the amount of mercaptoethanol produced is measured. The amount of mercaptoethanol is then compared to reference standard curves to determine the percentage of live cells in the sample or the viability of the cells.

6 Claims, 9 Drawing Sheets

(56) References Cited

OTHER PUBLICATIONS

Lee, Y.J., et al. "Enhancement of metabolic oxidative stress-induced cytotoxicity by the thioredoxin inhibitor 1-methylpropyl 2-imidazolyl disulfide is mediated through the ASK1-SEK1-JNK1 pathway." Mol Pharmacol. Dec. 2002;62 (6):1409-17.

Townsend, D.M., et al. "NOV-002, a glutathione disulfide mimetic, as a modulator of cellular redox balance." Cancer Res. Apr. 15, 2008;68(8):2870-7.

Sittadjody, S., et al. "Cell-secific redox pathways can be targeted using disulfides to induce cell death: Enhancement by low pH and quercetin." Proceedings of the American Association for Cancer Research Annual. Apr. 2007;48:559-560, #2356.

Reinhart, F.E., et al. "The anti-tumor activities in vitro of 5-imino-1,2,4-dithiazolidin-3-thione and bis (diethylthiocarbamoyl) disulfide toward the krebs-2 ascites carcinoma." Journal of the Franklin Institute. Jan. 1958;265 (1):58-62.

\* cited by examiner

METHOD OF DETERMINING CELL NUMBER OR VIABILITY USING HYDROXYETHYLDISULFIDE

This application is a national stage application of PCT/US2010/034899, filed on May 14, 2010, which claims priority under 35 U.S.C. §119(e) to U.S. Provisional Patent Application No. 61/178,929, filed on May 15, 2009; U.S. Provisional Patent Application No. 61/261,521, filed on Nov. 16, 2009; and U.S. Provisional Patent Application No. 61/290,084, filed on Dec. 24, 2009. Each of the foregoing applications is incorporated by reference herein.

This invention was made with government support under Grant Number CA109604 awarded by the National Institutes of Health. The government has certain rights in the invention.

FIELD OF THE INVENTION

The present invention relates to oxidative stress, cytotoxicity, and antioxidants. More specifically, assays for measuring oxidative stress and cytotoxicity and methods of use thereof are provided.

BACKGROUND OF THE INVENTION

Several publications and patent documents are cited throughout the specification in order to describe the state of the art to which this invention pertains. Each of these citations is incorporated herein by reference as though set forth in full.

Glucose-6-phosphate dehydrogenase (G6PD) is the first and rate-limiting enzyme of the oxidative pentose phosphate cycle (OPPC). Glucose, a substrate for the OPPC, is required for OPPC mediated detoxification of oxidants/disulfides. Glucose is utilized as a substrate by oxidative pentose phosphate cycle to generate reductants. These reductants are utilized to maintain reduced glutathione homeostasis in mammalian cells when exposed to oxidants/disulfides. Glutathione is a tripeptide consisting of glycine, cysteine and glutamate. The reduced glutathione (GSH) is up to 100 folds higher than the oxidized GSH (GSSG) in mammalian cells under normal conditions.

Oxidative stress is presently quantified by measuring the ratio of reduced glutathione (GSH) to oxidized glutathione (GSSG). Oxidized glutathione is the most commonly used biomarker in biomedical research. However, the various biochemical assays currently available require the preparation of tissue extracts and cannot be applied to humans because of their invasiveness. Indeed, while HPLC with electrochemical detection can monitor glutathione with better sensitivity than other biochemical assays, the method still requires tissue or cellular extracts. Furthermore, these assays may overestimate the extent of oxidative stress since depletion of GSH measured by biochemical assays may also include oxidation of GSH during lysis of cells and extract preparation. Moreover, none of these assays measures the function of GSH in live cells. In view of the foregoing, it is evident that there is a need for improved oxidative stress assays in live cells.

SUMMARY OF THE INVENTION

In accordance with one aspect of the instant invention, methods of measuring oxidative stress in a live cell are provided. In a particular embodiment, the methods comprise contacting cells with hydroxyethyldisulfide (HEDS) and determining the amount of extracellular mercaptoethanol, wherein the amount of extracellular mercaptoethanol is inversely proportional to the oxidative stress of the cell. In another embodiment, the amount of extracellular mercaptoethanol is directly proportional to the glutathione recycling capacity of the cell.

According to another aspect of the instant invention, methods of screening for an antioxidant are provided. In one embodiment, the methods comprise a) contacting a first cell with hydroxyethyldisulfide (HEDS); b) determining the amount of extracellular mercaptoethanol produced by the first cell; c) contacting a second cell with a compound; d) contacting the second cell with hydroxyethyldisulfide (HEDS); and e) determining the amount of extracellular mercaptoethanol produced by the second cell; wherein the presence of more extracellular mercaptoethanol from the second cell indicates that the compound is an antioxidant. In still another embodiment, the method comprises a) contacting a cell with a compound; b) contacting the cell with hydroxyethyldisulfide (HEDS); and c) determining the amount of extracellular mercaptoethanol produced by the cell, wherein the presence of more extracellular mercaptoethanol from the cell compared to a standard indicates that the compound is an antioxidant. In another embodiment, the first and second cells are from biological samples and the compound is administered to a subject.

In yet another aspect, methods of measuring the cytotoxicity of a compound are provided. The methods may comprise contacting cells with the compound, contacting the cells with hydroxyethyldisulfide (HEDS), and determining the amount of extracellular mercaptoethanol for the cells; wherein a decrease in the amount of extracellular mercaptoethanol for the cells compared to cells not exposed to the compound indicates that the compound is cytotoxic. In a particular embodiment, the method comprises obtaining a biological sample from a subject, administering the compound to the subject, and obtaining a second biological sample from the patient. The cells of the first and second biological samples are then contacted with hydroxyethyldisulfide (HEDS) and the amount of extracellular mercaptoethanol is determined.

According to still another aspect, kits for practicing the methods of the instant invention are provided. In a particular embodiment, the kits comprise a) 5,5-dithiobis 2-nitrobenzoic acid (DTNB); b) hydroxyethyldisulfide (HEDS); and c) sulfosalicyclic acid buffer (SSA). The kits may also comprise at least one of: DTNB buffer, HEDS buffer, 96-well plate(s), and reaction buffers containing glucose-6-phosphate dehydrogenase, thioredoxin reductase, thioredoxin or other antioxidants.

BRIEF DESCRIPTION OF THE DRAWINGS

FIGS. 1A and 1B are HPLC chromatograms obtained from the extracellular medium after 2 hours incubation of human cells with (FIG. 1B) and without (FIG. 1A) HEDS. FIG. 1A shows only a solvent peak (peak 1) for extracellular medium from cells incubated for 2 hours without HEDS. FIG. 1B shows a solvent peak (peak 1), a mercaptoethanol (ME) peak (peak 2), and a HEDS peak (peak 3) for extracellular medium from cells incubated for 2 hours with HEDS.

FIGS. 2A and 2B show a solvent peak (peak 1), a ME peak (peak 2), and a HEDS peak (peak 3) for extracellular medium from human cells incubated with HEDS for 2 hours after 24 hours treatment with and without arsenite. The results show that 10 µM arsenite (FIG. 2B) decreased the ME peak (peak 2) by almost 70% with a corresponding increase in the HEDS peak (peak 3) compared to the cells not treated with arsenite (FIG. 2A). Chromatograms without HEDS for these samples showed only a solvent peak.

FIG. 6 demonstrates that the instant assay can be used to measure the toxicity induced by cisplatin in human cells. The results show a ciplatin dose dependent decrease in HEDS conversion measured 5 days after overnight incubation of cells with micromolar (0, 10, 20, 30, 40, or 50 µM) concentrations of cisplatin.

DETAILED DESCRIPTION OF THE INVENTION

Glucose is converted into glucose-6-phosphate by hexokinase. Glucose-6-phosphate is used as a substrate by G6PD/oxidative pentose phosphate cycle to produce NADPH. NADPH is used as a cofactor to reduce disulfides into monosulfides, which are released into the medium. This conversion is dependent on the glucose level and active metabolic pathway of live cells.

In a particular embodiment, the assay of the instant invention use hydroxyethyldisulfide (HEDS), a unique non-toxic disulfide, to measure glucose dependent metabolic activity of live cells in vitro. The survival of cells is directly proportional to the conversion of HEDS into mercaptoethanol (ME) by metabolically active live cells. Dead cells fail to convert HEDS into mercaptoethanol. Accordingly, the assays of the instant invention generally encompass contacting cells (e.g., live cells) with HEDS and then monitoring or measuring the amount of extracellular ME. The amount of ME produced from HEDS can be measured in the extracellular medium since ME is extruded out quickly into the extracellular medium. Extracellular ME may be measured, for example, by a dithiobiznitrobenzoic acid (DTNB) assay or High Performance Liquid Chromatography/Electrochemical Detection (HPLC/EC): The cells of the assay may be any cell that produces NADPH, particularly mammalian cells and yeast. The percentage of live cells may be determined by the amount of ME produced.

The general assay of the instant invention may be used in a variety of methods. For example, the assay may be used 1) to screen for oxidative stress in live cells, 2) as a cell survival assay, 3) to screen for the toxicity of a compound, 4) to screen for exposure to or the presence of a toxin such as arsenical compounds, 5) to screen for toxicity or stress in subjects treated with cancer chemotherapeutic agents and/or radiation, 6) to measure glutathione recycling, 7) to screen the efficacy of an antioxidant or composition, 8) high throughput screening of chemicals/drugs that target biological molecules involved in cell survival, 9) to screen for tumor cell resistance to radiation and/or chemotherapeutic reagents, and 10) to predict radiation and/or chemotherapeutic response using blood samples from a subject. These methods are described in more detail below.

In accordance with one aspect of the instant invention, methods for measuring oxidative stress in a live cell are provided. The method comprises contacting the cells with HEDS and subsequently measuring the amount of extracellular ME, wherein the amount of extracellular ME is inversely proportional to oxidative stress. The method may further comprise obtaining a biological sample comprising the cells from a subject. In a particular embodiment, the method comprises obtaining at least one biological sample comprising cells from a subject, administering at least one compound to the subject, obtaining at least one second biological sample from the subject, and determining the amount of extracellular ME after HEDS administration. An increase in the extracellular ME from the second biological sample indicates that the at least one compound reduces oxidative stress. Additionally, while the instant methods comprise obtaining a first and second biological sample, the instant invention also encompasses a method wherein only at least one biological sample(s) are obtained after administration of the compound and the amount of extracellular ME after HEDS administration is compared to a standard(s) (e.g., the amount of extracellular ME after HEDS administration in a biological sample from a subject(s) not administered the compound). While the method is exemplified above with administering at least one compound to the subject, the method may also be used to measure toxicity after any challenge (e.g., after treatment with/exposure to radiation, chemotherapeutic agents, cytotoxins, and the like).

In accordance with another aspect of the instant invention, methods to quantify the survival/viability of cells are provided. As stated herein, cell death is directly proportional to the lack of conversion of HEDS into ME. In a particular embodiment, the method comprises contacting the cells with HEDS and subsequently measuring the amount of extracellular ME, wherein the amount of extracellular ME is proportional to cell viability. Optionally, a standard curve of extracellular ME production to viable cell number can be generated prior to testing an unknown sample.

Currently, there are four major assays commonly used as cell death/survival assays. However, there are substantial problems with these cell viability and cytotoxic assays. The cell survival assay of the instant invention overcomes the problems associated with these assays.

The first major assay is the lactose dehydrogenase (LDH) assay. This assay measures the release of LDH after membrane damage caused by cytotoxic drugs. One problem with this assay is that it requires collection of extra cellular medium at different time points since it is not known at what time the membrane leak occurs after cytotoxic treatment. The assay may also not be sensitive enough to detect low level of cell death. Further, most cytotoxins kill cells by intracellular mechanisms without damaging the plasma membrane and the assay only works for cytotoxins that induce high cell lysis within a short time. There is also a need to determine the peak response time after treatment for this assay and the peak response may vary at different concentrations of cytotoxins. Lastly, cells need to be grown in special medium without low serum since LDH in the serum will interfere with this assay.

A second major assay is the glucose consumption dependent $H_2O_2$ assay. This assay measures glucose consumption, which is proportional to the number of cells. The problem with this assay is that most cells consume glucose at a very slow rate and most medium has 25 mM glucose. If the medium has high concentration of glucose, there is a need to dilute the medium and errors may occur.

The third major assay is the (3-(4,5-dimethylthiazol-2-yl)-2,5-diphenyltetrazolium bromide) (MTT) assay. Purple formazan is formed by mitochondrial reduction of MTT in living cells. MTT, however, is not water-soluble and needs to be solubilized by DMSO. Furthermore, there may be interference from the medium, especially if the medium color changes when cells are confluent or when there is a change in pH of the medium.

Lastly, the fourth major assay is the sodium 3'-[1-(phenylaminocarbonyl)-3,4-tetrazolium]-bis(4-methoxy-6-nitro benzene sulfonic acid hydrate (XTT). A colored formazon product is formed by reduction of XTT. As with the MTT assay, there may be interference from the medium if the medium color changes when cells are confluent or there is a change in the pH of the medium. The XTT assay also requires phenazine methosulfate (PMS) to effectively reduce XTT. However, PMS is a known generator of oxygen free radicals, which causes potassium loss in cells. The reduction of XTT is solely dependent on NADH. More specifically, the reduction of XTT is caused by NADH released into the extracellular medium through trans-plasma membrane electron transport. The amount of extracellular reduction is not as effective as intracellular bioreduction. Furthermore, studies in yeast had shown that several factors such as iron and membrane enzymes other than NADH may also be responsible for bioreduction of XTT, thereby interfering with the assay.

In accordance with another aspect of the instant invention, methods for measuring the cytotoxicity of at least one compound are provided. In a particular embodiment, the method comprises providing at least two populations of cells wherein one population of cells has been contacted with the at least one compound and a second population of cells as a control which has not been contacted with the at least one compound. The method further comprises contacting the populations of cells with HEDS and subsequently measuring the amount of extracellular ME. A reduction in the extracellular ME from the population of cells contacted with the at least compound indicates that the at least one compound is cytotoxic. While the method is exemplified above with contacting the cells with at least one compound, the method may also be used to measure viability after any challenge (e.g., after treatment with radiation, chemotherapeutic agents, cytotoxins, and the like). The method may be used with high throughput screening of compounds. In a particular embodiment, the compound is a drug such as chemotherapeutics or anti-yeast, fungal or bacterial drugs.

In accordance with another aspect of the instant invention, the assay of the instant invention is used for high throughput screening of chemicals/drugs that target glucose 6-phosphate dehydrogenase, thioredoxin reductase, thioredoxin, or other antioxidants. In one embodiment, the method comprises contacting purified glucose 6-phosphate dehydrogenase, thioredoxin reductase, thioredoxin, or other antioxidants with HEDS and subsequently measuring the amount of extracellular ME in a reaction mixture. In a particular embodiment, the method comprises providing at least one compound selected from the group consisting of glucose 6-phosphate dehydrogenase, thioredoxin reductase, thioredoxin, and other antioxidant, in a reaction mixture (e.g., in a 96-well plate) wherein this reaction mixture has been contacted with at least one test compound (e.g., from a chemical library). The method further comprises contacting this mixture with HEDS and subsequently measuring the amount of ME. A decrease in ME indicates that the at least one compound possesses inhibitory effect on the target molecules such as glucose-6-phosphate dehydrogenase, thioredoxin reductase, thioredoxin, or other antioxidants.

In another embodiment of the instant aspect, the method comprises obtaining a biological sample comprising cells from a subject, administering at least one compound to the subject, obtaining a second biological sample from the subject, and determining the amount of extracellular ME after HEDS administration. A reduction in the extracellular ME from the second biological sample indicates that the at least one compound is cytotoxic. As stated hereinabove, the method may alternatively comprise obtaining at least one biological sample after administration of the compound and comparing to a standard(s). While the method is exemplified above with administering at least one compound to the subject, the method may also be used to measure toxicity after any challenge (e.g., after treatment/exposure with radiation, chemotherapeutic agents, cytotoxins, and the like).

In yet another embodiment of the instant aspect, the method may be used to screen for compounds which promote or increase cell survival. For example, the method may comprise contacting one of the populations of cells with at least one compound and, optionally, maintaining the cells under conditions which cause cell death, and then measuring extracellular ME after HEDS administration.

In accordance with another aspect of the instant invention, methods of detecting exposure to or the presence of a toxin, particularly an oxidative stress inducing toxin, are provided. In a particular embodiment, the method comprises contacting cells with HEDS and subsequently measuring the amount of extracellular ME. The method may comprise obtaining a biological sample comprising cells from a subject, optionally a subject suspected of having been exposed to the toxin. In a particular embodiment, the method comprises obtaining an environmental sample (e.g., a water and/or soil sample) and contacting the sample with HEDS and subsequently measuring the amount of ME. In still another embodiment, cells are contacted (e.g., cultured) with the environmental sample prior to contacting with HEDS. The lack of HEDS conversion in the instant assays correlates (e.g., indicates an increased risk/likelihood) with toxin (e.g., arsenical, radiation, chemotherapeutic agent, etc.) induced GSH depletion and cell death. Thus, the inhibition of HEDS conversion is an effective biomarker of oxidative stress that can be used to detect (or indicate an increased risk for) exposure to or the presence of toxins such as arsenicals. The method may also comprise comparing the extracellular ME to a standard (e.g., a biological sample obtained from a subject known not have been exposed to the toxin or exposed to a known toxin; or other samples (e.g., environmental sample) comprising a known amount of the toxin). In a particular embodiment, the toxin is an arsenical compound, pollutant, mercury, cadmium, lead, asbestos, barium, carbon tetrachloride, chloromethane, chromium, copper, dichloroethene (DCE), polychlorinated biphenyls (PCBs), polycyclic aromatic hydrocarbons (PAHs), selenium, silver, sulfuric acid, tetrachloroethene (PCE), trichloroethane (TCA), trichloroethene (TCE), vinyl chloride, zinc, acetaldehyde, acetonitrile, acrylamide, acrylic acid, aniline, 1,1'-biphenyl, 1-butanol, butraldehyde, carbon disulfide, carbonyl sulfide, chlorine, chlorobenzene, cyclohexane, 1,4-dioxane, freon 113, methanol, methyl ethyl ketone, methyl isobutyl ketone, methyl methacrylate, methyl-tert-butyl ether, methylchloroform (1,1,1-Trichloroethane), methylene chloride(dichloromethane), 2-methoxyethanol, nitrobenzene, perchloroethylene, phthalic anhydride, styrene, toluene, trichlorobenzene, or 1,2,4-trimethylbenzene. In a particular embodiment, the toxin is an arsenical compound.

Arsenicals are the most common contaminants in soil, ground water, food, and plants. More than 15 million people in the U.S. and around 100 million in the rest of the world are likely to be exposed to arsenicals. Arsenicals are known to cause oxidative stress, which may be responsible for the toxic, carcinogenic, and mutagenic effects of arsenicals in humans and animals. Arsenicals are also known to cause atherosclerosis, cancer, and other diseases in humans. Inorganic arsenic commonly exists as arsenate ($As^{5+}$) and arsenite ($As^{3+}$) in ground water. Oxidation of $As^{3+}$ to $As^{5+}$ may increase the $As^{5+}$ content in the soil. The semi-metallic form of arsenic oxidizes rapidly in air, and at high temperatures produces arsenic trioxide. In addition, arsenic trioxide is currently used in humans to treat cancer. Phenylic arsenic compounds are the main contaminants in groundwater at abandoned sites with a history of arsenic containing chemical weapon agents. Exemplary arsenicals include, without limitation, sodium arsenate, sodium arsenite, arsenic trioxide and phenylarsine oxide, as these arsenicals are environmental pollutants. These arsenicals can cause oxidative stress leading to lipid peroxidation, protein oxidation, and depletion of glutathione (GSH) and other antioxidants in mammalian cells. Herein, it has been determined that the toxicity of arsenic compounds is dependent on the extent of inhibition of HEDS conversion in cells.

In accordance with another aspect of the instant invention, methods for measuring the glutathione recycling capacity of a live cell are provided. The method comprises contacting the live cells with HEDS and subsequently measuring the amount of extracellular ME. It has been demonstrated that glutathione (GSH) recycling (GSH→GSSG→GSH) is important for cellular defense against oxidative stress. An assay that measures the capacity of cells to recycle glutathione, rather than just measuring GSH and GSSG, is more appropriate in determining metabolic oxidative stress since GSH recycling covers the total metabolic oxidative stress. The conversion of HEDS requires GSH recycling by converting GSSG, which is produced during HEDS conversion, back to GSH. Defects in GSH recycling in cells affect the conversion of HEDS into mercaptoethanol. The assay of the instant invention is not only useful for laboratory based biomedical research (e.g., tissue culture and animals) but also for use on subjects.

In accordance with another aspect of the instant invention, the assay of the instant invention can be used to investigate the antioxidant property of at least one compound (e.g., dietary and antioxidant supplements). The method comprises contacting the cells with HEDS and subsequently measuring the amount of extracellular ME. In a particular embodiment, the method comprises providing at least two populations of cells wherein one population of cells has been contacted with the at least one compound and a second population of cells as a control which has not been contacted with the at least one compound. The method further comprises contacting these populations of cells with HEDS and subsequently measuring the amount of extracellular ME. An increase in the extracellular ME from the population of cells contacted with the at least compound indicates that the at least one compound possess antioxidant properties. In a preferred embodiment, the method comprises obtaining a biological sample comprising cells from a subject, administering at least one compound to the subject, obtaining a second biological sample from the subject, and determining the amount of extracellular ME after HEDS administration. An increase in the extracellular ME from the second biological sample indicates that the at least one compound is an antioxidant.

According to another aspect of the instant invention, methods of screening tumor cells resistance to chemotherapeutic agents and radiation are provided. In one embodiment, the methods comprise a) contacting a first tumor cell with hydroxyethyldisulfide (HEDS); b) determining the amount of extracellular mercaptoethanol produced by the first tumor cell; c) contacting a second tumor cell with hydroxyethyldisulfide (HEDS); and d) determining the amount of extracellular mercaptoethanol produced by the second tumor cell; wherein the presence of more extracellular mercaptoethanol from the first or second cell indicates that the tumor cell with higher capacity to convert hydroxyethyldisulfide (HEDS) into mercaptoethanol is resistant/less responsive to cancer therapy. In another embodiment, the first and second tumor cells are from biological samples from a subject. Additionally, while the instant methods comprise obtaining a first and second biological sample, the instant invention also encompasses a method wherein only a first tumor sample is obtained and the amount of extracellular ME after HEDS administration is compared to a standard(s) (e.g., the capacity of other tumor cells and, optionally, non-tumor cells) to convert HEDS and their known responsiveness (e.g., ability to treat, effectiveness of treatment, and/or dosage requirement) to a particular cancer therapy.

According to another aspect of the instant invention, methods of screening blood antioxidant capacity to predict response of a subject to chemotherapeutic agents and/or radiation are provided. In one embodiment, the methods comprise a) contacting a first blood sample with hydroxyethyldisulfide (HEDS); b) determining the amount of extracellular mercaptoethanol produced by the first blood sample; c) contacting a second blood sample with hydroxyethyldisulfide (HEDS); and d) determining the amount of extracellular mercaptoethanol produced by the second blood sample; wherein the presence of more extracellular mercaptoethanol from the first or second blood sample indicates that the subject with higher capacity to convert hydroxyethyldisulfide (HEDS) into mercaptoethanol is resistant/less responsive to cancer therapy. In another embodiment, the first and second blood sample may consist of whole blood, individual blood cells, or serum from a subject. Additionally, while the instant methods comprise obtaining a first and second blood sample, the instant invention also encompasses a method wherein only a first blood sample is obtained and the amount of extracellular ME after HEDS administration is compared to a standard(s) (e.g., the capacity of other blood samples (e.g., blood samples from those undergoing treatment) to convert HEDS and their known responsiveness (e.g., ability to treat, effectiveness of treatment, and/or dosage requirement) to a particular cancer therapy).

According to yet another aspect of the instant invention, methods of screening blood for HEDS bioreductive capacity to predict the treatment outcome of a subject are provided. In a particular embodiment, the subject has at least one disease or disorder. Exemplary diseases or disorders include, without limitation, cardiovascular diseases, atherosclerosis, neurological disorders, inflammatory diseases, kidney disease, adult respiratory distress syndrome, autoimmune disease, liver disease, Alzheimer's disease, Parkinson's disease, ageing and ageing related diseases, allergies, lung disease, diabetes, coronary artery disease, digestive disease, concussion, over-exercise (exhaustion), drug use (e.g., in athletes), and any disease associated with oxidative stress. In one embodiment, the methods comprise a) contacting a first blood sample from the subject with hydroxyethyldisulfide (HEDS); b) determining the amount of extracellular mercaptoethanol produced by the first blood sample; c) contacting a second blood sample (e.g., from a normal subject) with hydroxyethyldisulfide (HEDS); and d) determining the amount of extracellular mercaptoethanol produced by the second blood sample; wherein the presence of less extracellular mercaptoethanol from the first blood sample indicates that the subject with lower capacity to convert hydroxyethyldisulfide (HEDS) will have poor(er) outcome from the treatment and may require additional antioxidant therapy. In another embodiment, the first and second blood sample may consist of whole blood, individual (isolated) blood cells, or serum from a subject. Additionally, while the instant methods comprise obtaining a first and second blood sample, the instant invention also encompasses a method wherein only a first blood sample is obtained and the amount of extracellular ME after HEDS administration is compared to a standard(s) (e.g., the capacity of other blood samples (e.g., blood samples from a normal subject or those undergoing treatment) to convert HEDS and optionally their known responsiveness (e.g., ability to treat, effectiveness of treatment, and/or dosage requirement) to a particular therapy).

According to still another aspect of the instant invention, methods of screening blood for HEDS bioreductive capacity to predict the susceptibility of a subject to at least one disease or disorder are provided. Exemplary diseases or disorders include, without limitation, cardiovascular diseases, atherosclerosis, neurological disorders, inflammatory diseases, kidney disease, adult respiratory distress syndrome, autoimmune disease, liver disease, Alzheimer's disease, Parkinson's disease, ageing and ageing related diseases, allergies, lung disease, diabetes, coronary artery disease, digestive disease, concussion, over-exercise (exhaustion), drug use (e.g., in athletes), and any disease associated with oxidative stress. In one embodiment, the methods comprise a) contacting a first blood sample from the subject with hydroxyethyldisulfide (HEDS); b) determining the amount of extracellular mercaptoethanol produced by the first blood sample; c) contacting a second blood sample (e.g., from a normal subject, a subject with said disease, or subject known to be at risk for said disease) with hydroxyethyldisulfide (HEDS); and d) determining the amount of extracellular mercaptoethanol produced by the second blood sample; wherein the presence of less extracellular mercaptoethanol from the first or second blood sample indicates that the subject with lower capacity to convert hydroxyethyldisulfide (HEDS) into mercaptoehtanol is susceptible to disease. In another embodiment, the first and second blood sample may consist of whole blood, individual (isolated) blood cells, or serum from a subject. Additionally, while the instant methods comprise obtaining a first and second blood sample, the instant invention also encompasses a method wherein only a first blood sample is obtained and the amount of extracellular ME after HEDS administration is compared to a standard(s) (e.g., the capacity of other blood samples (e.g., blood samples from a normal subject, a subject with said disease or a subject known to be at risk for said disease) to convert HEDS and optionally their known risk for developing said disease).

The instant invention also encompasses diagnostic/prognostic methods. In a particular method, the method comprises determining the responsiveness of a tumor to a particular treatment and/or determining the response of a subject to a particular treatment (e.g., chemotherapy and/or radiation) as described hereinabove. Upon determining the responsiveness of a tumor and/or the impact on a subject, the practitioner can determine whether the particular treatment is to be administered to the patient or whether a new type of treatment should be sought. The practitioner may also determine the dosing level of the treatment needed to treat the disorder (e.g., cancer), while minimizing any negative impact on the patient. For example, if it is determined that the tumor would not be responsive to the treatment, then a new treatment may be sought or higher doses may be required/tested. If it is determined that the subject would be adversely affected by the treatment, then a new treatment may be sought or a lower dosage of the treatment may be administered.

DEFINITIONS

As used herein, the term "oxidative stress" refers to the cytotoxic effects of oxygen radicals (e.g., superoxide anion ($O_2^-$), nitric oxide, hydroxy radical (OH), and hydrogen peroxide ($H_2O_2$)), generated, for example, as byproducts of metabolic processes that utilize molecular oxygen (see e.g., Coyle et al., Science 262:689-695 (1993)). In other words, oxidative stress may refer to a loss of redox homeostasis (imbalance) with an excess of reactive oxidative species (ROS) by the process of oxidation. Oxidative stress may refer to a state of a cell or tissue of an animal, in vitro or in vivo.

As used herein, the term "antioxidant" refers to compounds that neutralize the activity of reactive oxygen species or inhibit the cellular damage done by the reactive species or their reactive byproducts or metabolites. The term "antioxidant" may also refer to compounds that inhibit, prevent, reduce or ameliorate oxidative reactions. Examples of antioxidants include, without limitation, vitamin E, vitamin C, ascorbyl palmitate, vitamin A, carotenoids, beta carotene, retinoids, xanthophylls, lutein, zeaxanthin, flavones, isoflavones, flavanones, flavonols, catechins, ginkgolides, anthocyanidins, proanthocyanidins, carnosol, carnosic acid, organosulfur compounds, allylcysteine, alliin, allicin, lipoic acid, omega-3 fatty acids, eicosapentaeneoic acid (EPA), docosahexaeneoic acid (DHA), tryptophan, arginine, isothiocyanates, quinones, ubiquinols, butylated hydroxytoluene (BHT), butylated hydroxyanisole (BHA), super-oxide dismutase mimetic (SODm), and coenzymes-Q.

The terms "reactive oxygen species," or "oxidative species," as used herein, refer to oxygen derivatives from oxygen metabolism or the transfer of electrons, resulting in the formation of "free radicals" (e.g., superoxides or hydroxyl radicals).

As used herein, the terms "host," "subject," and "patient" refer to any animal, including humans.

As used herein, a "biological sample" refers to a sample of biological material obtained from a subject, preferably a human subject, including a tissue, a tissue sample, a cell sample, a tumor sample, and a biological fluid (e.g., blood or urine). Preferably, the biological sample is obtained by in the least invasive manner (e.g., a swab or blood draw).

A "carrier" refers to, for example, a diluent, matrix, adjuvant, preservative (e.g., Thimersol, benzyl alcohol), anti-oxidant (e.g., ascorbic acid, sodium metabisulfite), solubilizer (e.g., Tween 80, Polysorbate 80), emulsifier, buffer (e.g., Tris HCl, acetate, phosphate), antimicrobial, bulking substance (e.g., lactose, mannitol), excipient, auxilliary agent or vehicle with which an active agent of the present invention can be maintained. Carriers can be sterile liquids, such as water and oils, including those of petroleum, animal, vegetable or synthetic origin. Water or aqueous saline solutions and aqueous dextrose and glycerol solutions may be also employed as carriers.

As used herein, "diagnose" refers to assessing, evaluating, and/or prognosing the disease status (progression, regression, stabilization, response to treatment, etc.) in a patient known to have the disease.

As used herein, the term "prognosis" refers to providing information regarding the impact of the presence of a disease on a subject's future health (e.g., expected morbidity or mortality, the likelihood of developing disease, and the severity of the disease). In other words, the term "prognosis" refers to providing a prediction of the probable course and outcome of the disease and/or the likelihood of recovery from the disease and/or responsiveness to a particular treatment.

Assay

In accordance with the instant invention, methods for measuring oxidative stress are provided. In a particular embodiment, the method comprises:

a) providing cells;
b) contacting the cells of step a) with HEDS;
c) measuring the amount of extracellular ME, wherein a the amount of extracellular ME is inversely proportional to the amount of oxidative stress. The cells of step a) may be obtained from a subject (e.g., a human). In another embodiment, the cells of step a) are contained within a biological sample, preferably blood, obtained from a subject. In another embodiment, the cells of step a) are established normal human or rodent cells or other types of cells with and without oxidative pentose phosphate cycle. In another embodiment, the cells of step a) are established rodent or human cancer cells or cancer cells from other species with and without oxidative pentose phosphate cycle. The cells of the biological sample may be isolated and/or washed prior to contacting with HEDS.

The method may also comprise comparing the amount of extracellular ME from a test sample with at least one standard. For example, the standard may be the amount of extracellular ME from cells (e.g., from a subject) which is healthy and/or does not have oxidative stress. The standard may also be the amount of extracellular ME from cells (e.g., from a subject) which are experiencing oxidative stress.

In a particular embodiment, the methods of the instant invention comprise adding HEDS and the ME-detecting reagent, optionally after a desired amount of time, to the cells without harvesting of the cells, washing, or removal of the medium. In another embodiment, HEDS is added to the cells and the cells are incubated for a desired amount of time (e.g., 0.25, 0.5, 1, 2, 3, or more hours) before at least a portion of the extracellular medium is removed and the extracellular ME is measured (e.g., by HPLC) or the ME-detecting reagent is added after processing the samples with sulfosalicyclic acid (SSA) buffer.

In a particular embodiment, the ME detecting agent is DTNB. In yet another embodiment, the amount of ME is measured via O.D. (e.g., the O.D. can be read directly on a microtiter plate (MTP) by a MTP reader). The methods of the instant invention may be performed on microtiter plates (e.g., 96, 24, and 6 well plates) or 100 mm plates.

The amount of extracellular ME can be measured by any technique. In another embodiment, the amount of ME is measured by High Performance Liquid Chromatography/Electrochemical Detection (HPLC/EC). For example, samples may be analyzed using a HPLC system comprising a C18 column and a mobile phase of 50 mM phosphate, pH 2.7 with octane sulfonic acid (0.05 mM) and 2.2% acetonitrile. In a preferred embodiment, the extracellular ME is measured by a 5,5-dithiobis 2-nitrobenzoic acid (DTNB) assay (see, e.g., Ayene et al. (2002) J. Biol. Chem., 277:9929-35). For example, extracellular media may be mixed with DTNB and then the O.D. may be measured at 412 nm. The concentration may be calculated using an extinction coefficient of $1.36 \times 10^4$ for reduced DTNB.

Unlike the LDH assay described hereinabove, the method of the instant invention does not require time kinetics as the time for end point is known and constant. Furthermore, the optical density for 20,000 cells for the instant assay without HEDS and measured 144 hours after plating is 0.24, indicating that the background from medium is very low. In contrast, the optical density for 20,000 cells after incubating the cells with HEDS for 3 hours and measured 144 hours after plating is 3.2, thereby indicating a spread of 2.7. Therefore, the noise to signal ratio of the instant invention is 15, thereby indicating significant sensitivity.

While HEDS is exemplified herein, any disulfide containing compound may be used in the methods of the instant invention. Disulfide containing compounds are readily available (see, e.g., Sigma Aldrich 2006-2007 catalog). In one embodiment, the disulfide containing compounds are di-alkyl disulfides (e.g., disulfides of lower alkyls (i.e., containing 1-4 carbons) comprising at least one sulfur atom) or di-aryl disulfides, wherein the members of the disulfide can be the same (symmetrical disulfide) or different (asymmetrical disulfide). In another embodiment, the disulfide containing compounds are disulfides comprising thiamine, such as, without limitation, thiamine disulfide, thiamine propyl disulfide, and thiamine tetrahydrofuryl disulfide. In another embodiment, exemplary disulfide containing compounds include, without limitation, hydroxyethyldisulfide (HEDS; a disulfide of mercaptoethanol (ME)), disulfide of mercaptopropionylglycine (MPG), disulfide of MPG and a lower alkyl, disulfide of MPG and ME, disulfide of mesna (2-sulfanylethanesulfonate), disulfide of MPG and mesna, and disulfide of ME and mesna. In a preferred embodiment, the disulfide containing compound is HEDS.

Kit

Kits for performing the methods of the instant invention are also provided. In a particular embodiment, the kits comprise 1) HEDS and 2) DTNB. In another embodiment, at least one of HEDS and DTNB is contained within a composition comprising a carrier. In still another embodiment, the kit comprises a) 5,5-dithiobis 2-nitrobenzoic acid (DTNB); b) hydroxyethyldisulfide (HEDS); and, optionally, c) sulfosalicyclic acid buffer (SSA). The kits of the instant invention may further comprise at least one of: a) HEDS buffer; b) DTNB buffer; and c) reaction buffer containing at least one of glucose-6-phosphate dehydrogenase, thioredoxin reductase, thioredoxin, or other antioxidants. In yet another embodiment, the kit further comprises at least one of: microtiter plate(s), buffers (e.g., sulfosalicyclic acid buffer (SSA)), tubes, reaction buffer(s) (e.g., reaction buffers containing glucose-6-phophate dehydrogenase, thioredoxin reductase, thioredoxin, or other antioxidants), and instruction material.

The example set forth below is provided to better illustrate certain embodiments of the invention. It is not intended to limit the invention in any way.

Example

Figure 1A:
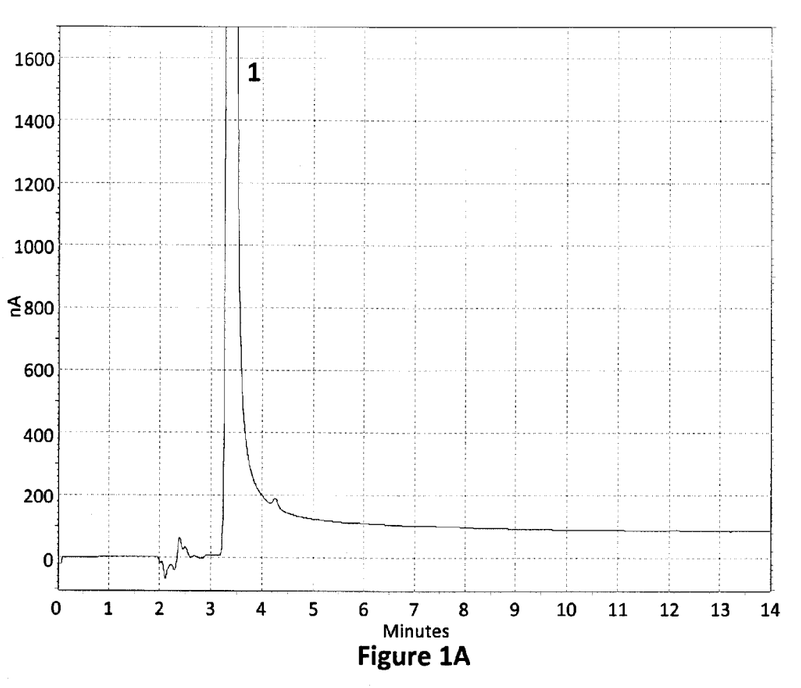
FIGS. 1A and 1B demonstrate the conversion of HEDS into mercaptoethanol (ME) by human cells as determined by High Performance Liquid Chromatography (HPLC)/electrochemical analysis.
Figure 1B:
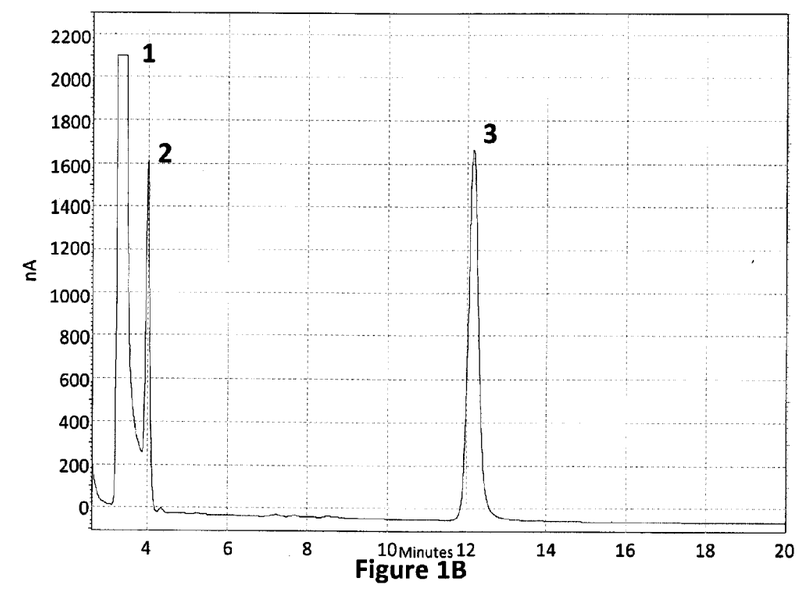
Figure 2A:
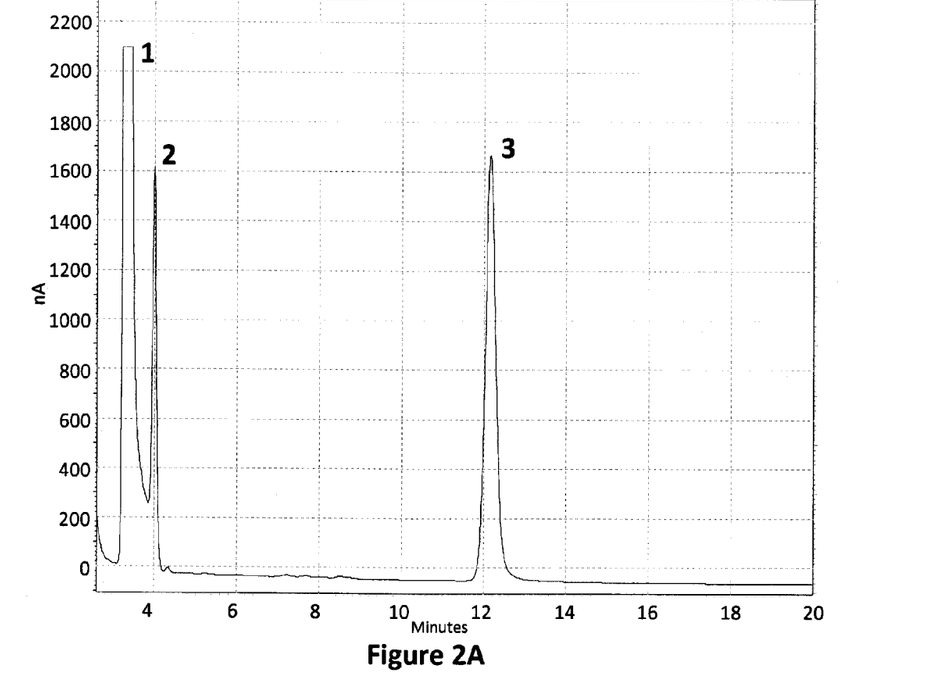
FIGS. 2A and 2B depict the measurement of arsenite induced oxidative stress in human cells in vitro as measured by HPLC/electrochemical analysis of extracellular medium samples. HPLC chromatograms for human cells incubated with 0 (FIG. 2A) and 10 µM (FIG. 2B) arsenite for 24 hours in vitro are provided.
Figure 2B:
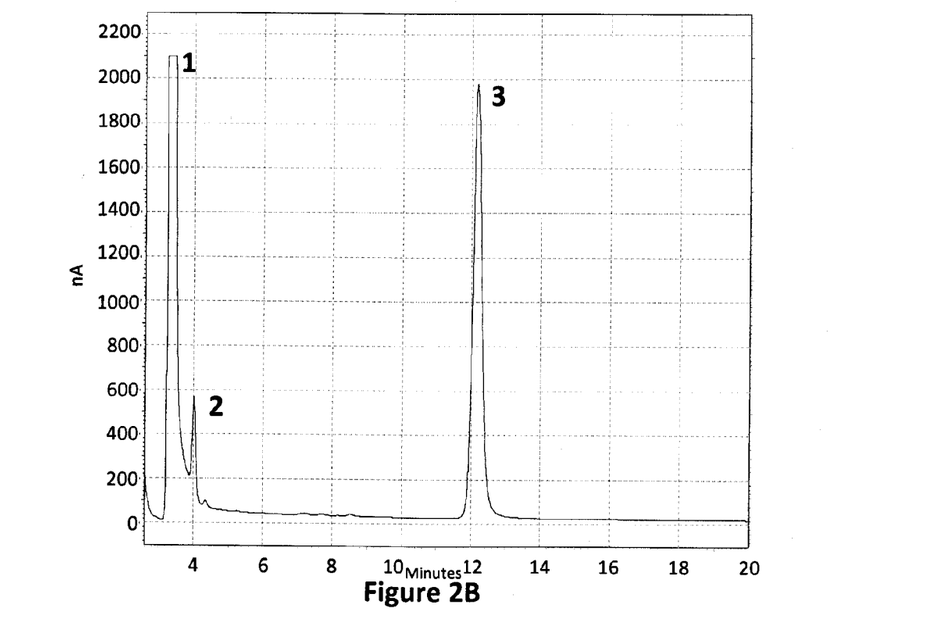

In live cells, HEDS is reduced to mercaptoethanol, a free sulfhydryl containing compound, with no toxic effect on cells suggesting a rapid reduction by intracellular antioxidants. The ME produced inside the cells is extruded into the extracellular medium. This conversion mediated by the antioxidant system can be measured in the extracellular medium without the need for cellular extract. HPLC electrochemical detector was used to quantify the conversion of HEDS into mercaptoethanol in mammalian cells in tissue culture. FIG. 1 shows the HPLC peaks obtained from the extracellular medium after 2 hours incubation of human cells with HEDS. In the absence of HEDS, the extracellular medium did not have any detectable amount of mercaptoethanol. However, the extracellular medium showed a large HPLC peak for ME in 2 hours after incubation of HEDS. This HPLC/electrochemical detection system is dependent on the GSH recycling capacity of mammalian cells. Similar chromatograms were also obtained for extracellular medium from rodent cells incubated with and without HEDS. These results indicate that the instant assay is specific for the conversion of HEDS into ME and can be used for human, rodent and other cell types. FIG. 2 shows that the HPLC peaks obtained from the extracellular medium of human cells treated with arsenite, which induces oxidative stress, showed lack of conversion of HEDS into mercaptoethanol.

Figure 3:
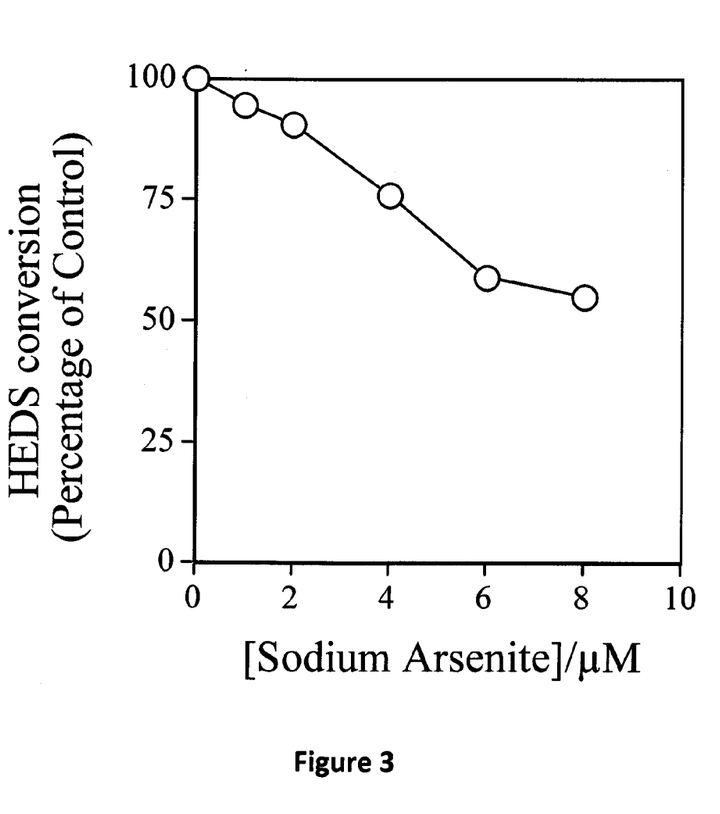
FIG. 3 is a graph of HEDS conversion measured by the HEDS/DTNB assay of the instant invention of the extracellular medium from human HCT116 cells treated with different concentrations of arsenite. The results in FIG. 3 show an arsenite concentration dependent decrease in HEDS conversion by human cells incubated with arsenite for 24 hours. HEDS conversion was measured immediately after the 24 hours incubation of cells with arsenite.

In order to determine the sensitivity of the instant assay (HEDS/DTNB) in measuring the oxidative stress induced by arsenite, the effect of micromolar concentrations of arsenite ranging from 0, 1, 2, 4, 6 and 8 µM was tested in human cells. FIG. 3 shows a linear arsenite concentration dependent inhibition of HEDS conversion measured by HEDS/DTNB assay using the extracellular medium from these cells. The results in FIG. 3 demonstrate that this assay is very sensitive in measuring the oxidative stress induced by arsenite, even at micromolar concentrations.

Figure 4:
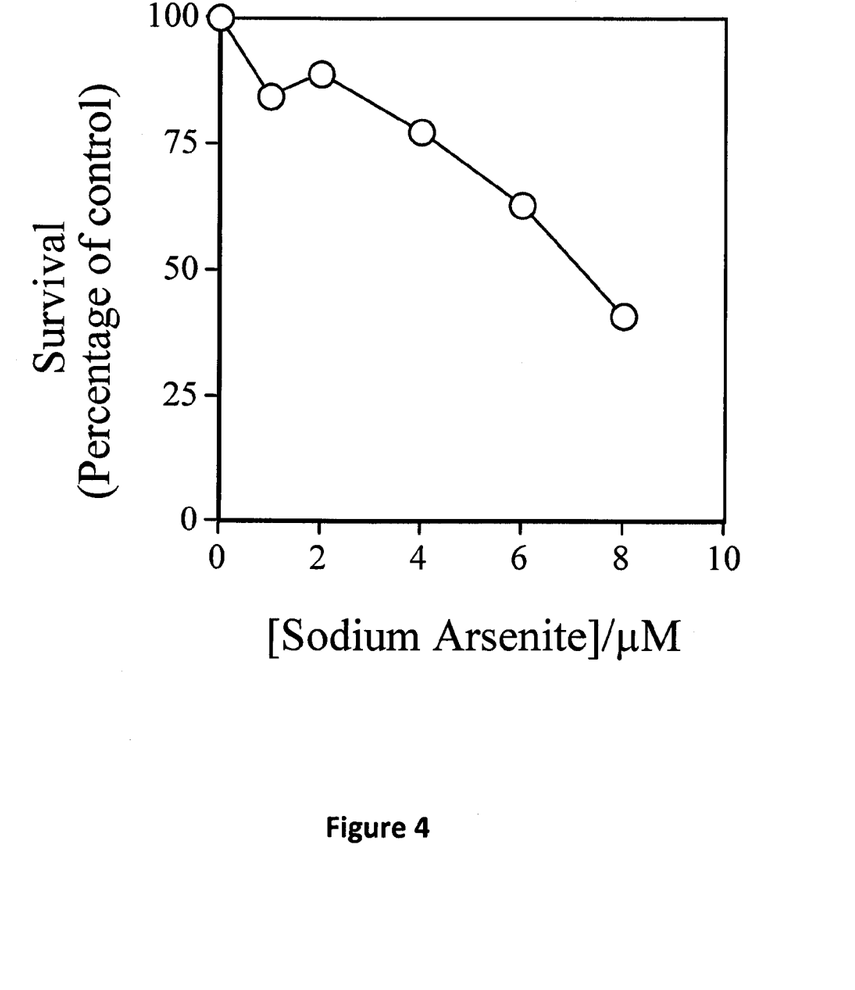
FIG. 4 is a graph of arsenite toxicity measured by Coulter Counter Analysis of cells harvested six days after arsenite treatment. The results in FIG. 4 demonstrate an arsenite concentration dependent decrease in the survival of human HCT116 cells incubated with arsenite for 24 hours. The cell growth was measured six days after removing the arsenite from the extracellular medium by washing the cells three times with fresh growth medium.

In order to determine whether the oxidative stress measured after 24 hours incubation of cells with arsenite serves as an indicator of toxicity/cell death, cell death was measured by Coulter Counter Analysis six days after the arsenite treatment. The results in FIG. 4 demonstrate an arsenite concentration dependent decrease in the survival of human HCT116 cells incubated with arsenite for 24 hours. The cell growth was measured six days after removing the arsenite from the extracellular medium by washing the cells three times with fresh growth medium using the methods followed by Ayene et al. (J. Biol. Chem. (2002) 277:9929-35). However, HEDS conversion (FIG. 3), which showed arsenite concentration dependent decrease, was measured immediately after 24 hours incubation with arsenite. Yet, HEDS conversion correlated with cell death, which was measured 6 days after the same 24 hours arsenite treatment. These results demonstrate that the novel HEDS conversion assay can also be an earlier predictor of arsenite toxicity in cells. This assay is the first to quantify oxidative stress induced by micromolar concentrations of arsenite.

Figure 5A:
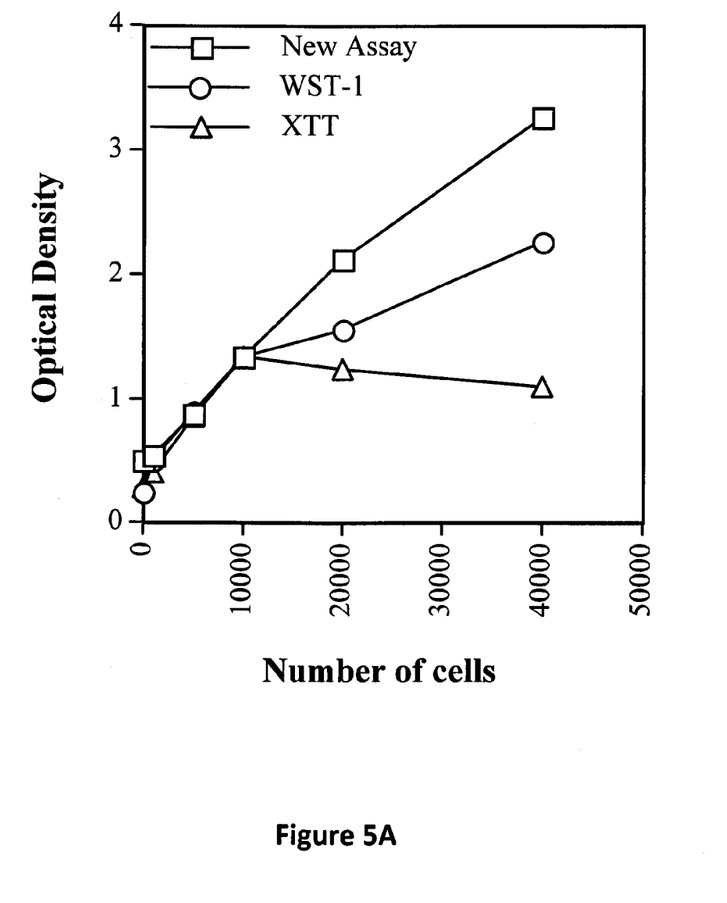
FIGS. 5A-5C are graphs of the application of the assay of the instant invention compared to other commercially available assays (WST-1 and XTT) used for cell survival in tissue culture medium. The figure shows a linear cell density dependent conversion of HEDS better than the commercially available assays (WST-1 and XTT) measured 16 hours after plating the cells in a 96 well microtiter plate. Cells tested: HCT116 cells (FIG. 5A), MCF10A cells (FIG. 5B), and MCF7 cells (FIG. 5C).
Figure 5B:
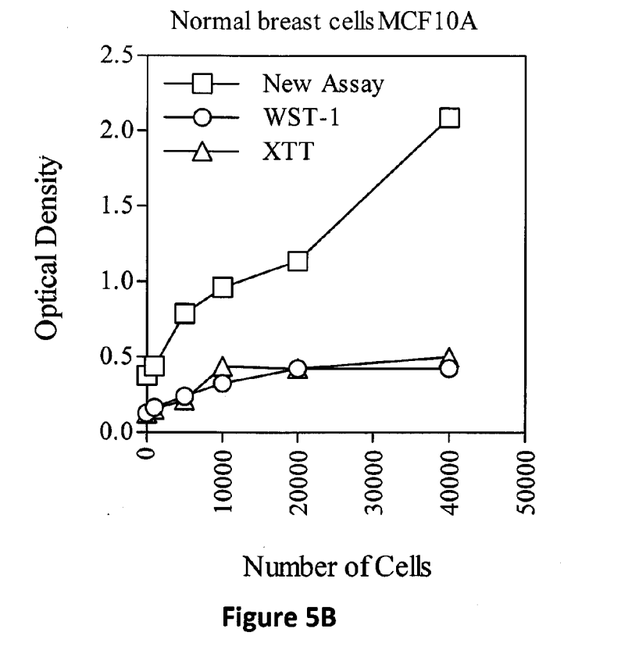
Figure 5C:
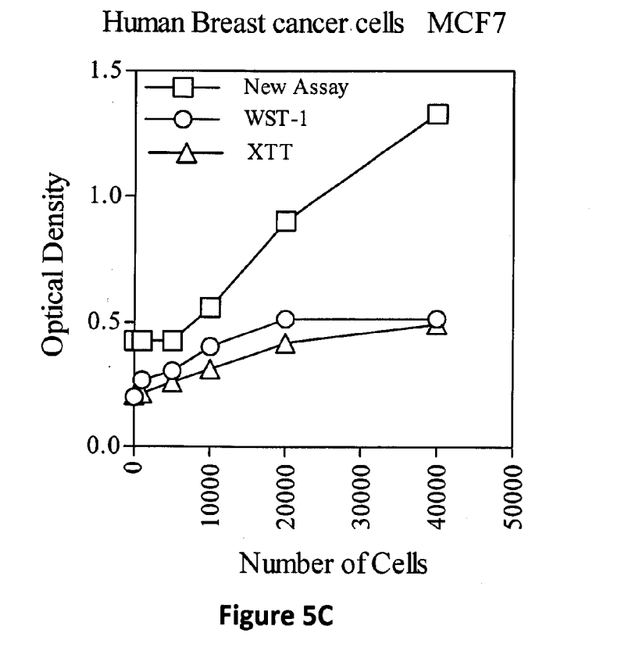

In order to determine whether this assay can be used for High Throughput Screening (HTS) to quantify metabolically active cells, the instant assay was compared with commercially available assays (XTT and WST-1) in a 96 well platform. The results in FIG. 5 demonstrate that the instant assay shows a linear cell concentration dependent response better than the XTT and WST-1. The assays for XTT and WST-1 were carried out as per the manufacturer's instructions. The assays were performed on a human colon carcinoma cell line (HCT116 cells; FIG. 5A), normal breast cells (MCF10A; FIG. 5B), and human breast cancer cells (MCF7; FIG. 5C).

Figure 6:
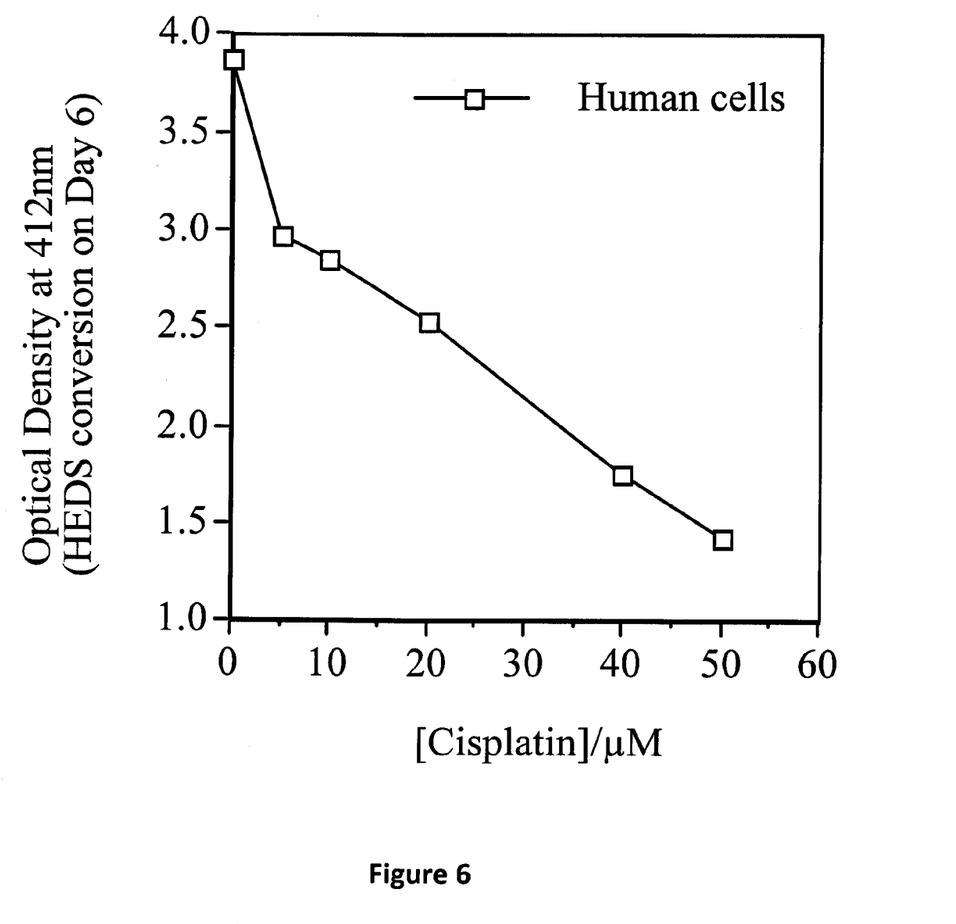
FIG. 6 is a graph showing the application of the assay of the instant assay to quantify the toxicity of cisplatin in human cells in a 96 well platform.

In order to determine whether the instant assay can be used for High Throughput Screening (HTS) to quantify the toxicity of cisplatin, the HEDS conversion by human cells five days after overnight incubation of cells with 0, 10, 20, 30, 40, and 50 µM of cisplatin was measured in a 96 well plate. The results in FIG. 6 demonstrate that the instant assay can be used to measure the toxicity induced by cisplatin in human cells in a 96 well plate format.

Figure 7A:
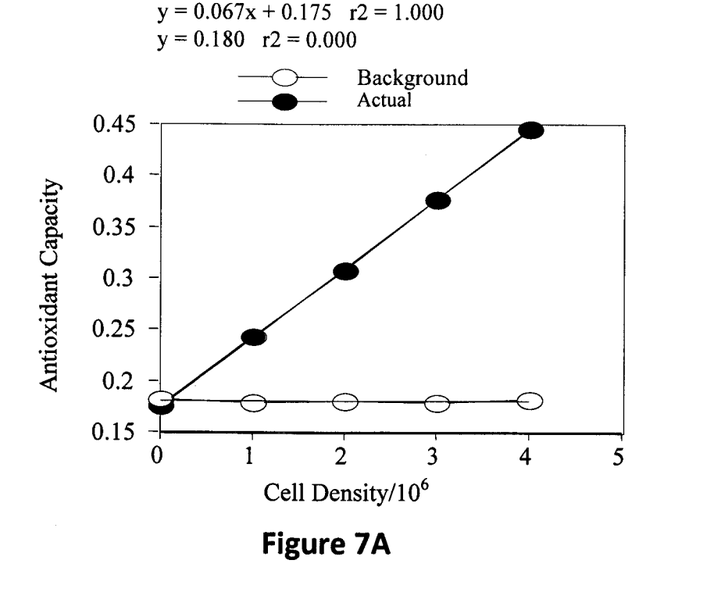
FIGS. 7A-7C are graphs of the total antioxidant capacity of various cell densities of three cell lines: Jurkat (FIG. 7A), CCRF-CEM (FIG. 7B), and T98G (FIG. 7C).
Figure 7B:
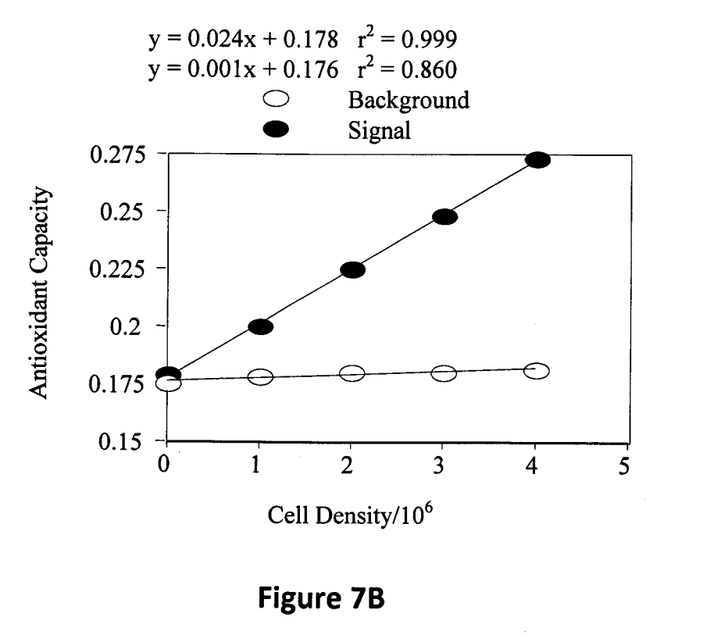
Figure 7C:
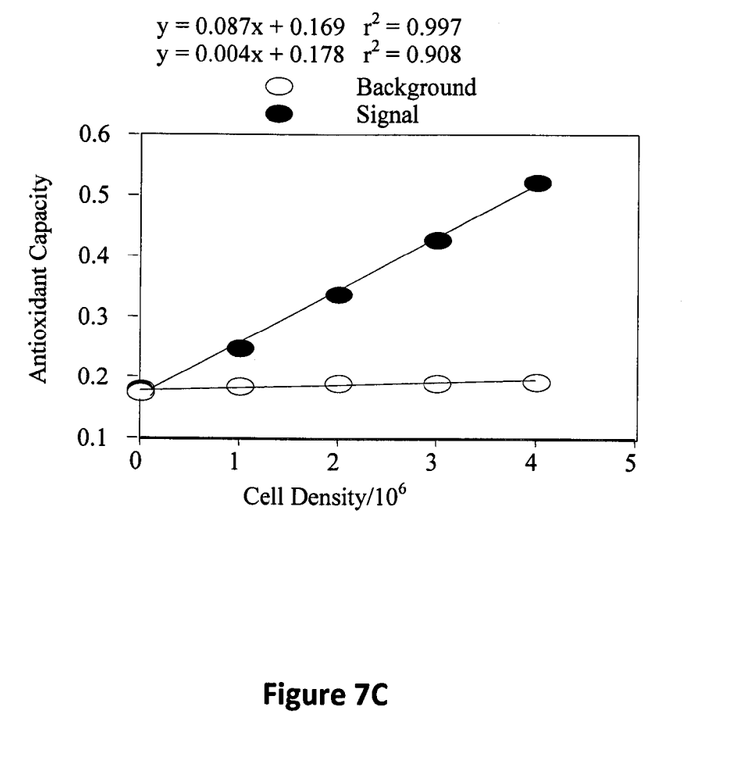

FIGS. 7A-7C show that the assay of the instant invention can be used to determine antioxidant capacity in any cell types. Indeed, a cell density dependent linear response for total antioxidant capacity was observed for T lymphocytes (Jurkat cells (FIG. 7A) and CCRF-CEM cells (FIG. 7B)) and glioma cells (T98G cells; FIG. 7C) with coefficient of determination values ($R^2$) ranging from 0.997 to 1.000.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method for determining the percentage of live cells in a sample, said method comprising:
  a) contacting said sample with hydroxyethyldisulfide (HEDS); and
  b) determining the amount of extracellular mercaptoethanol;
  c) calculating the percentage of live cells from the amount of mercaptoethanol produced using a standard curve of extracellular mercaptoethanol production to viable cell number.

2. The method of claim 1, wherein said sample is obtained from a subject.

3. The method of claim 1, wherein step b) comprises contacting extracellular fluid with 5,5-dithiobis 2-nitrobenzoic acid (DTNB).

4. A method for determining the percentage of live cells in a sample, said method comprising:
  a) contacting said sample with hydroxyethyldisulfide (HEDS); and
  b) determining the amount of extracellular mercaptoethanol;
  c) calculating the percentage of live cells from the amount of mercaptoethanol produced using the amount of extracellular mercaptoethanol produced by a standard sample of live cells.

5. The method of claim 4, wherein said sample is obtained from a subject.

6. The method of claim 4, wherein step b) comprises contacting extracellular fluid with 5,5-dithiobis 2-nitrobenzoic acid (DTNB).

* * * * *

UNITED STATES PATENT AND TRADEMARK OFFICE
CERTIFICATE OF CORRECTION

PATENT NO.        : 8,697,391 B2                                    Page 1 of 1
APPLICATION NO.   : 13/320602
DATED             : April 15, 2014
INVENTOR(S)       : Iraimoudi S. Ayene It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 13 days.

Signed and Sealed this

Twenty-ninth Day of September, 2015

Michelle K. Lee
*Director of the United States Patent and Trademark Office*